United States Patent
Li et al.

(10) Patent No.: US 7,801,613 B2
(45) Date of Patent: Sep. 21, 2010

(54) METAL INJECTION MOLDED TITANIUM ALLOY HOUSING FOR IMPLANTABLE MEDICAL DEVICES

(75) Inventors: Bernard Li, Plymouth, MN (US); Reginald D. Robinson, Plymouth, MN (US); John E. Kast, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 588 days.

(21) Appl. No.: 11/796,116

(22) Filed: Apr. 26, 2007

(65) Prior Publication Data

US 2008/0269829 A1 Oct. 30, 2008

(51) Int. Cl.
*A61N 1/375* (2006.01)

(52) U.S. Cl. ............ 607/36; 607/1; 607/2; 607/3; 607/4; 607/5; 607/37; 607/38

(58) Field of Classification Search ............ None
See application file for complete search history.

(56) References Cited

U.S. PATENT DOCUMENTS

| | | | |
|---|---|---|---|
| 4,041,955 A | | 8/1977 | Kelly et al. |
| 4,784,160 A * | | 11/1988 | Szilagyi ............ 607/116 |
| 5,913,881 A * | | 6/1999 | Benz et al. ............ 607/36 |
| 6,010,803 A * | | 1/2000 | Heller et al. ............ 429/175 |
| 6,360,749 B1 | | 3/2002 | Jayaraman |
| 6,500,187 B1 | | 12/2002 | Petersen |
| 6,800,326 B1 | | 10/2004 | Uchiyama |
| 7,012,799 B2 | | 3/2006 | Muffoletto et al. |
| 7,174,212 B1 * | | 2/2007 | Klehn et al. ............ 607/36 |
| 7,177,691 B2 * | | 2/2007 | Meadows et al. ............ 607/36 |
| 2006/0129240 A1 * | | 6/2006 | Lessar et al. ............ 623/17.14 |
| 2006/0285991 A1 * | | 12/2006 | McKinley ............ 419/36 |
| 2007/0178005 A1 * | | 8/2007 | Broadley et al. ............ 419/37 |

FOREIGN PATENT DOCUMENTS

| | | |
|---|---|---|
| WO | 0006327 | 2/2000 |
| WO | 2007112070 | 10/2007 |
| WO | 2008054439 | 5/2008 |

OTHER PUBLICATIONS

Material Properties of Ti-Al6-V4 ; from Granger.*

* cited by examiner

*Primary Examiner*—Carl H Layno
*Assistant Examiner*—Paula J Stice
(74) *Attorney, Agent, or Firm*—Scott A. Marks; Rick L. Franzen

(57) ABSTRACT

The housing of an implantable medical device is made of a titanium alloy that provides improved electrical performance, mechanical strength, and reduced MRI heating. The titanium alloy housing includes portions formed by metal injection molding and welded together. Wall thickness of at least a portion of one major face of the housing is reduced by chemical etching a metal injected molded housing portion.

34 Claims, 5 Drawing Sheets

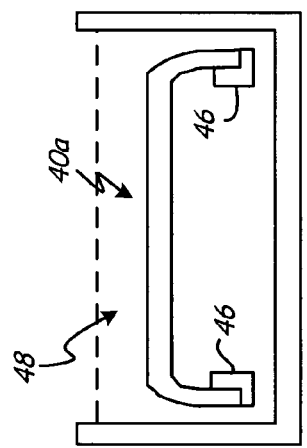
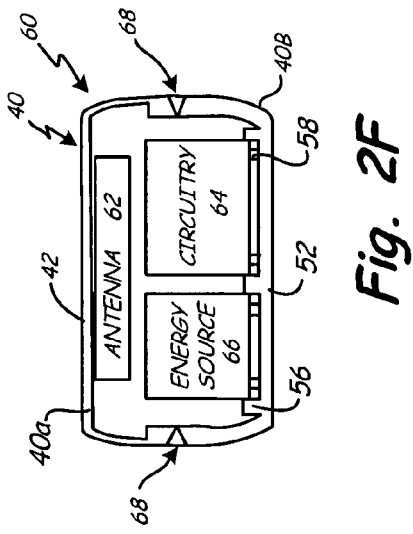
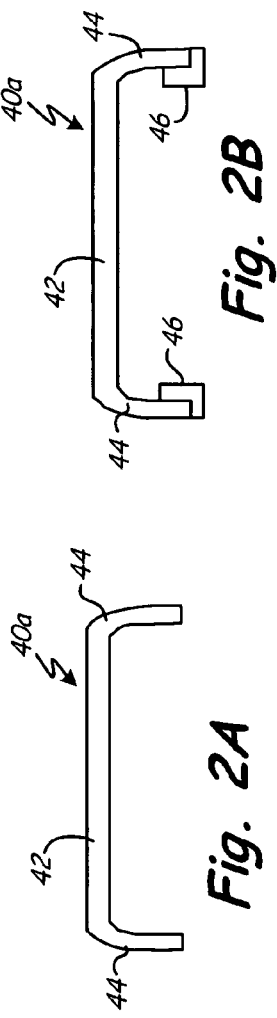
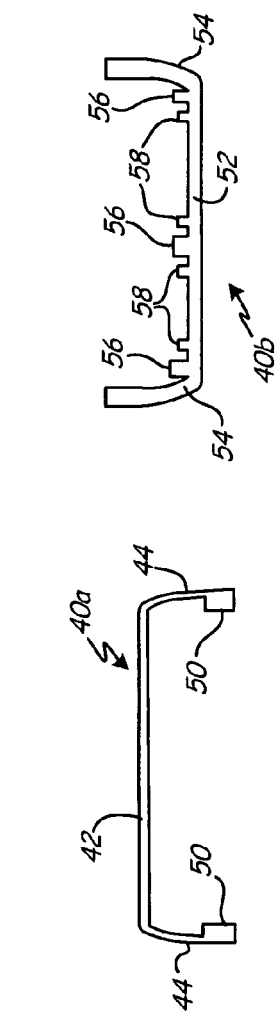

METAL INJECTION MOLDED TITANIUM ALLOY HOUSING FOR IMPLANTABLE MEDICAL DEVICES

BACKGROUND OF THE INVENTION

This invention relates to implantable medical devices (IMDs). In particular, the invention relates to the housing of an implantable medical device formed of a titanium alloy.

Implantable medical devices are used to produce therapeutic results in a patient and for monitoring physiologic parameters of a patient. Examples of IMDs include implantable drug infusion pumps, implantable neurostimulators, implantable cardioverter defibrillators, implantable cardiac pacemakers, and cochlear implants. Most of these IMDs either provide an electrical output or contain electrical circuitry to perform their intended functions. These devices are typically powered by a battery contained within the housing of the implantable medical device.

Since useful life of an IMD is dependent upon the operating life of the battery that provides power, the development of rechargeable power sources that can be charged using electromagnetic energy from outside the patient's body provides the opportunity for longer life IMDs. The ability to deliver electromagnetic energy to the charging circuitry within the IMD is affected by the electrical characteristics of the housing of the implantable medical device. Typically, implantable medical device housings are made of a biocompatible metal such as commercial pure (CP) titanium. To improve electrical performance of the recharging circuitry, a housing of a material having a higher resistivity than conventional CP titanium housings is desirable. A higher resistivity housing would also enhance telemetry to and from the IMD, and would reduce magnetic resonance imaging (MRI) heating effects when a patient with an IMD is subjected to an MRI procedure.

BRIEF SUMMARY OF THE INVENTION

The housing for an implantable medical device is formed of a titanium alloy having a resistivity of greater than about 100 μOhm-cm. The housing includes housing portions that are formed by metal injection molding and then joined together by welding.

BRIEF DESCRIPTION OF THE DRAWINGS

FIGS. 2A-2F illustrate steps of the method of FIG. 1.

DETAILED DESCRIPTION

An IMD housing made of a titanium alloy can provide improved electrical performance for both recharging and telemetry, improved mechanical properties such as tensile yield strength, and reduced MRI heating effects. A titanium alloy with a high resistivity (preferably in a range of about 100 μOhm-cm to about 220 μOhm-cm) offers better electrical performance than conventional metal housings of CP titanium. Titanium alloys containing aluminum, vanadium, and/or molybdenum, for example, have both higher resistivity and also higher tensile yield strength than pure titanium. The higher the resistivity of the alloy, the higher the tensile yield strength will be.

One barrier to use of titanium alloy housings is that high strength titanium alloys are difficult to roll into a thin sheet. As a titanium alloy has a higher alloy content (i.e. a higher content of elements such as aluminum, vanadium and molybdenum), the titanium alloy becomes more difficult to roll into thinner gauge and more difficult to form into the shapes required for an IMD housing. Higher resistivity (e.g. greater than 100 μOhm-cm) titanium alloys are particularly difficult to form into tight corners as required for a housing of an IMD. For some titanium alloys, cold forming to create a tight corner is not possible, and cold forming processes may not be available for thin sheets.

Another practical problem with use of titanium alloys for an IMD housing is the difficulty in obtaining high resistivity alloys. Primary usage of these alloys is in the aerospace industry. The total amount of titanium alloy material that could be required for IMD housings is very small compared to the requirements of the aerospace industry. Therefore, the formulation of special titanium alloy compositions and the rolling of the alloy to thin gauge needed to make IMD housings is problematic.

Figure 1:
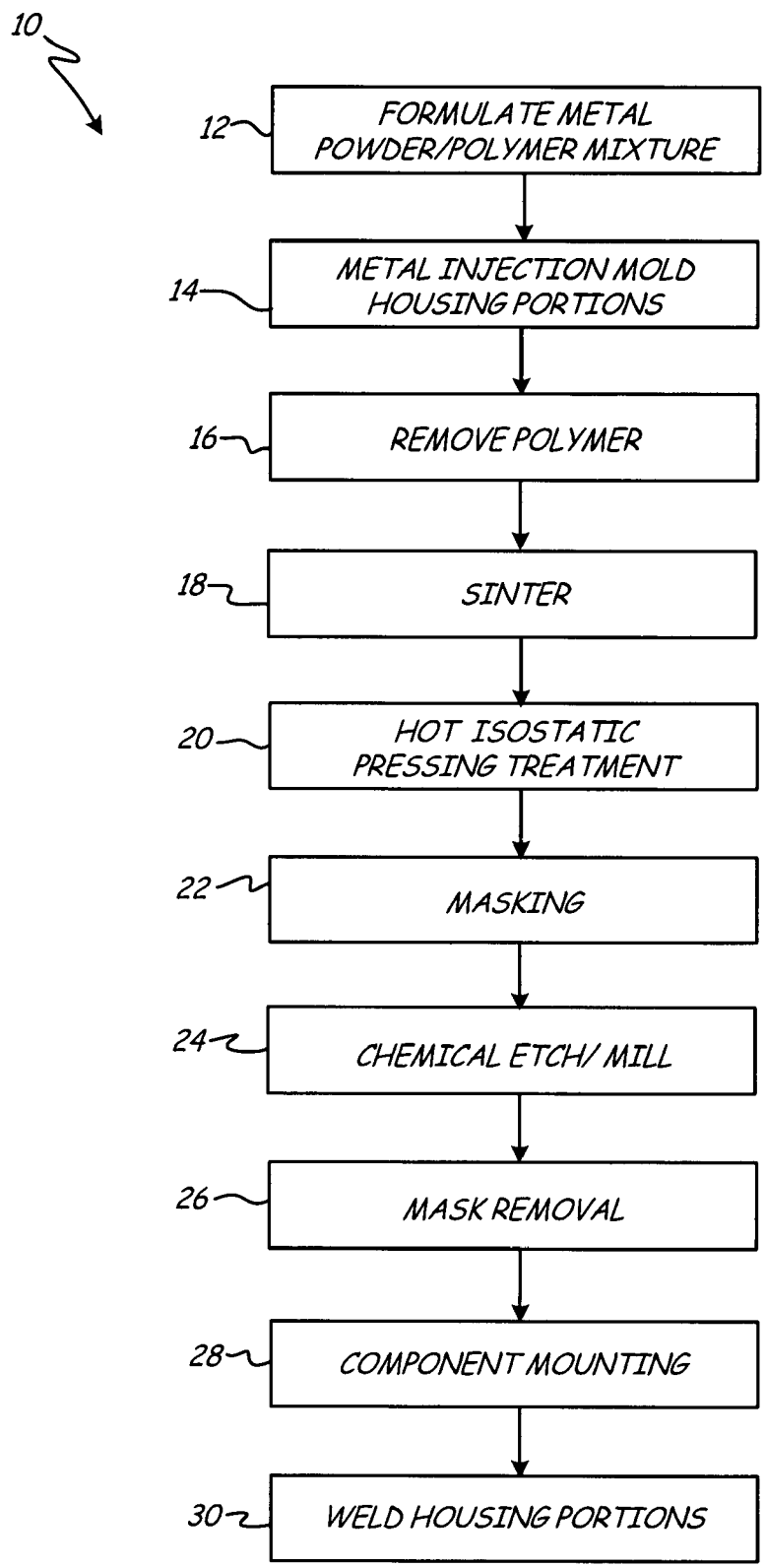
FIG. 1 is a flow diagram of a method of forming a high strength, high resistivity titanium alloy IMD housing.

FIG. 1 is a diagram of IMD housing fabrication process 10, which overcomes these problems by using metal injection molding (MIM) to form titanium alloy IMD housings. Metal injection molding (MIM) processes involve the injection of a mixture of fine metal particles and a hot liquid polymer into a metal die, in a manner similar to plastic injection molding. The MIM process can make parts with complex shapes, tight tolerances, and tight radius curvatures.

Process 10 begins by formulating a mixture of metal powders and polymer (step 12). Using a MIM process, a titanium alloy housing can be formed with whatever alloy composition is desired. The alloy powder can be made of a mixture of powders of the individual metal constituents (such as titanium, aluminum, vanadium, molybdenum, etc.). The composition of the alloy is determined by the percentage of the different constituent powders.

The metal powder/polymer mixture is then injected into the mold cavities of the die to form two or more housing portions that will be joined together to form the IMD housing (step 14). The housing portions may be two halves that are identical in shape, or may have different shapes that mate together to form the IMD housing. Metal injection molding of the housing portions will produce green parts containing both polymer and metal powder.

The green parts are then subjected to a process to remove most of the polymer, through heating and/or immersion in a suitable solvent, in liquid or vapor form (step 16). The resulting metal parts are then sintered to a high density, typically about 95 percent (step 18). The metal alloy of the housing portions is further consolidated from about 95 percent density to about 99 percent density using a Hot Isostatic Pressing (HIP) treatment (step 20).

One shortcoming of the MIM process is that the minimum wall thickness of the molded parts is on the order of about 0.020 inch to about 0.030 inch. To achieve desired electrical properties, the wall thickness of one or both of the major faces of the IMD housing should be less than about 0.015 inch, and preferably on the order of about 0.008 to about 0.012 inch.

Selective thinning of walls that require a reduced wall thickness is achieved by masking the housing portions (step 22). The masking step is followed by a chemical etching or milling process 24 that etches the exposed areas requiring reduced wall thickness (step 24). For example, the wall thickness of a major face of the housing which will have an antenna coil mounted against its inner surface will be etched, while the rim of the housing portion may have a greater wall thickness to facilitate laser welding with the other housing portion(s). After the chemical etching or milling process, the mask is removed.

The housing portions are then ready to have electrical components mounted. These components can include an antenna coil, a rechargeable energy source, and electrical circuitry that processes sensed signals, delivers therapy, and communicates through telemetry with external devices. To facilitate component mounting (step 28), molded bosses, standoffs, shelves, recesses, cavities, ribs or other support structures for the components to be mounted may be formed on inner surfaces of the housing portions as part of the metal injection molding. In addition, molded features may also be formed on external surfaces of the housing.

When the components have been assembled within the respective housing portions, the portions are positioned adjacent one another, and are welded together (step 30). This welding process may be performed, for example, by laser welding.

The MIM process also permits the addition of other additives to further tailor the electrical or mechanical properties of the housing. For example, higher resistivity can be achieved by adding ceramic particles, such as titanium carbide, titanium dioxide, or silicon carbide to the alloy powders that are injected into the mold.

The MIM process also allows the housing to achieve shapes that are not possible using wrought material. For example, tight radius curvatures that conventional forming processes cannot achieve are possible using the MIM. Complex shapes and additional internal structures to hold components of the IMD can be formed an integral part of the housing using the MIM process. Due to the near net shape nature of housing portions made by the MIM process, there is very low waste of the alloy material.

Although MIM produces wall thicknesses that are greater than those needed to provide the desired electrical characteristics, process 10 achieves the needed wall thicknesses. Selective material removal, such as by chemical etching, reduces wall thicknesses after formation of the housing portions by MIM.

FIGS. 2A-2F show an example of fabrication of an IMD housing using method 10 of FIG. 1. In this example, IMD housing 40 include two housing portions or halves 40a, 40b. In FIGS. 2A-2D, housing half 40a is illustrated, while FIG. 2E shows housing half 40b. FIG. 2F shows halves 40a and 40b joined together by welding.

FIG. 2A shows housing half 40 after it has been formed as a green part by metal injection molding, heated to remove polymer, sintered, and consolidated by HIP treatment (steps 14-20). Housing half 40a includes major face 42 and sidewalls 44, which define an inverted cup in FIG. 2A. The wall thickness of housing half 40a as formed by the MIM process is greater than 0.020 inch and may be greater than 0.030 inch. As a result, the wall thickness of housing half 40a, and in particular the wall thickness of face 42, must be reduced.

In FIG. 2B, mask 46 has been applied on the inner wall and bottom of sidewalls 44. The remainder of housing half 40a is left exposed. Mask 46 can be in the form of tape, paint, or photoresist, for example.

In FIG. 2C, housing half 40a has been placed in an acidic etching solution 48. Chemical milling thins walls of housing half 40a at those surfaces that are not covered by mask 46.

FIG. 2D shows housing half 40a after chemical milling has been completed and mask 46 has been removed. As shown in FIG. 2D, the wall thickness of main face 42 as well as portions of sidewalls 44 has been reduced to a thickness that will provide favorable transmission of electromagnetic energy for recharging of the energy source of the IMD, and for telemetry. The wall thickness of main face 42 may be, for example, in a range of about 0.008 to about 0.012 inch Rim section 50 has a greater wall thickness, which is useful for welding together of the housing halves.

FIG. 2E shows housing half 40b after metal injection molding and subsequent processing (steps 14-20). Housing half 40b includes major face 52, sidewalls 54, and molded mounting structures (ribs 56 and bosses 58) on the inner surface of main face 52. In this example, housing half 40b does not require selective wall thinning like housing half 40a.

FIG. 2F shows IMD 60 after internal components such as antenna 62, circuitry 64, and energy source 66 have been mounted to housing halves 40a and 40b. In this simplified example, housing halves 40a and 40b are joined together at their rim sections by laser weld 68.

Figure 3:
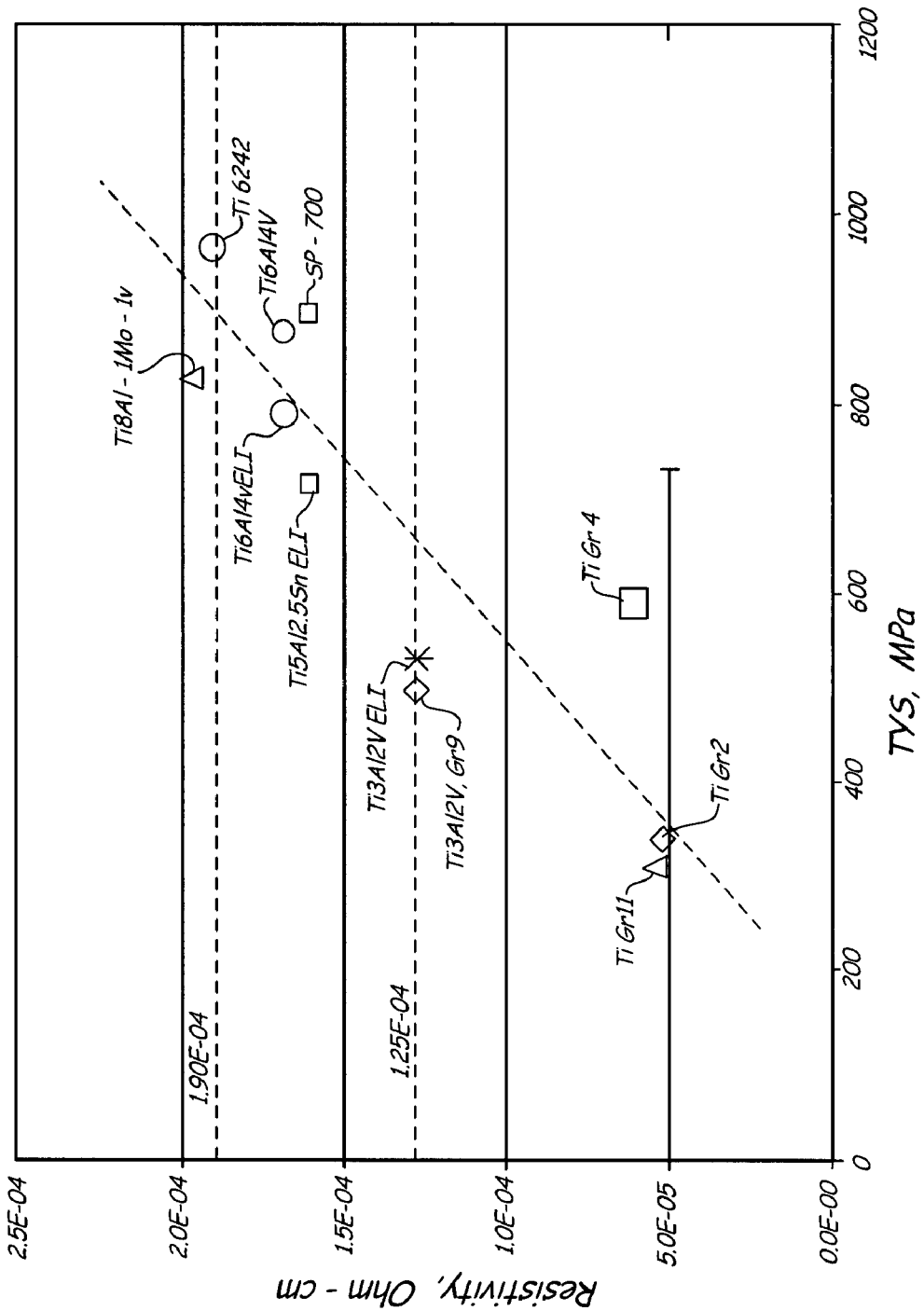
FIG. 3 is a graph of resistivity and tensile yield strengths of titanium and titanium alloys.
Figure 4:
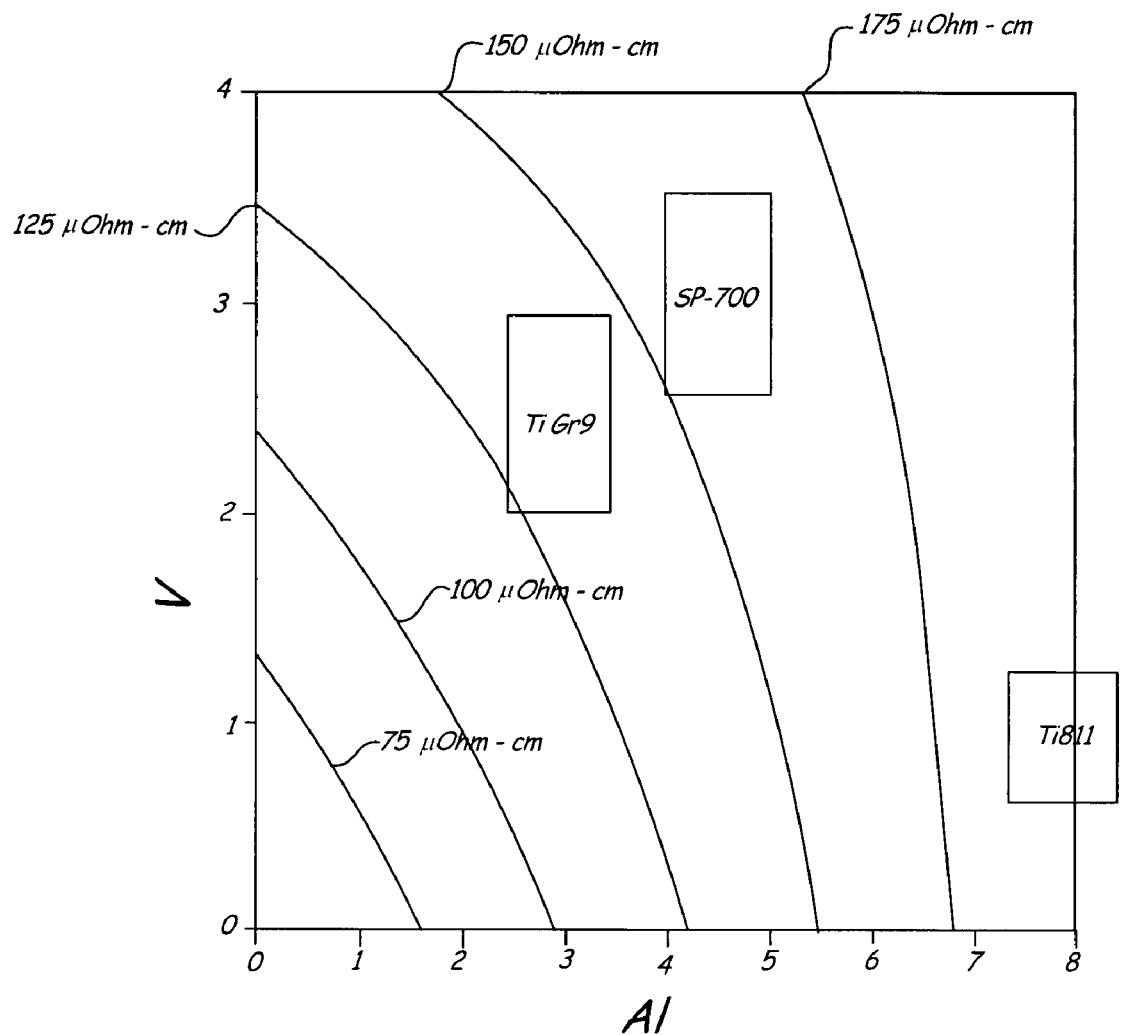
FIG. 4 is a contour plot of resistivity of a titanium alloy as a function of aluminum and vanadium content.

The use of metal injection molded titanium alloy housings offers significantly improved properties, as illustrated in FIGS. 3 and 4. FIG. 3 is a graph showing resistivity and tensile yield strength of pure titanium and various titanium alloys. FIG. 4 is a contour plot of resistivity as a function of aluminum and vanadium content in titanium alloys. The composition ranges of three specific alloys (TiGr9, SP-700, and Ti811) are shown. Titanium alloys offer increased tensile yield strength and increased resistivity when compared to pure titanium.

Alloys having resistivity in range of about 100 μOhm-cm to about 220 μOhm-cm, and preferably about 125 μOhm-cm to about 190 μOhm-cm, provide improved electrical properties in a titanium alloy IMD housing. In particular, an IMD housing made from an alloy having a resistivity of 125 μOhm-cm or greater can result in improved recharging efficiency (on the order of about 8 dB power coupling increase for frequencies over 50 kHz). The increased resistivity of the titanium alloy IMD housing also improves telemetry by increasing the transmit and receive distances, and decreases temperatures induced under MRI. In this range, tensile yield strength of the titanium alloys also increases as resistivity increases.

For those alloys having a resistivity of about 170 μOhm-cm and greater, the tensile yield strengths of the alloys (which may be greater than about 500 Mpa) make it impractical to use rolling, cold-forming or hot-forming process to form the alloys with the dimensions required for an IMD housing. The use of MIM to form housing portions, and the selective reduction of wall thickness by chemical etching or milling, makes use of these alloys possible for IMD housings.

The mechanical strength of the titanium alloys allows wall thicknesses of IMD housings made using MIM processing to be reduced. As shown in FIG. 3, a threefold increase in tensile yield strength can be achieved with titanium alloys relative to pure titanium. The increased yield strength allows thinner walls, which enhances recharging efficiency and telemetry characteristics.

The titanium alloys used for IMD housings are preferably α Ti or near α Ti alloys. In comparison, α Ti and near α Ti alloys have higher resistivity than β Ti alloys.

Figure 5:
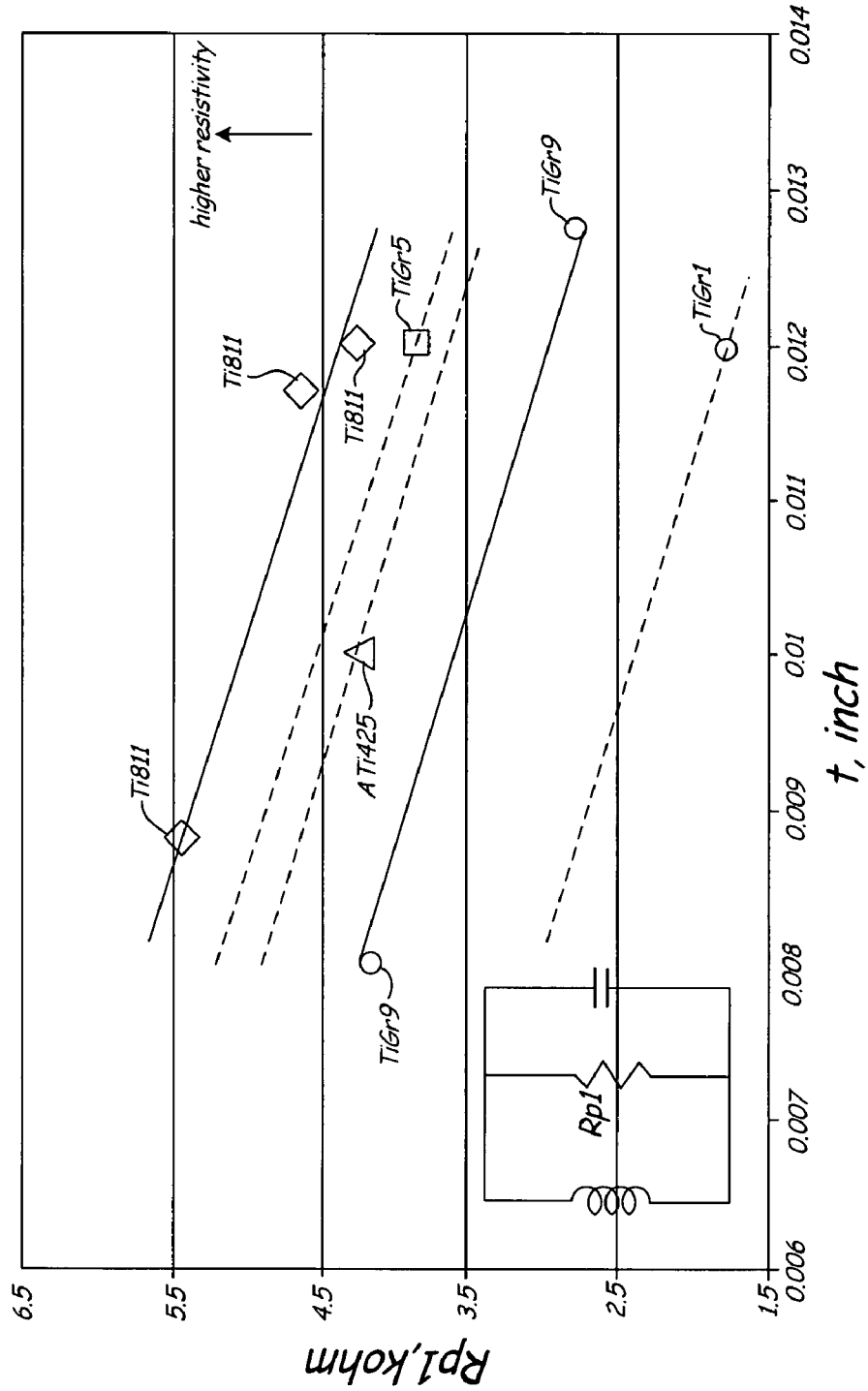
FIG. 5 is a graph of effective parallel coil resistance of titanium and titanium alloy housings with different housing wall thicknesses.

FIG. 5 shows a graph of effective resistance (RP1) of titanium and titanium alloy housings. The importance of resistivity and wall thickness of the major faces of the IMD housing is to increase the effective resistance created by the housing wall adjacent to the antenna coil. As illustrated in FIG. 5, increases in resistance can be achieved by increasing the resistivity of the material forming the housing wall, as well as reducing the wall thickness. The combination of higher resistivity and higher tensile yield strength make titanium alloys particularly attractive. As shown in FIG. 5, at approximately the same wall thickness (0.012 inch) as a titanium housing wall, titanium alloys offer significantly higher effective resistance. The much higher tensile yield strength of the titanium alloys allow reduced wall thickness without compromising mechanical strength. As a result, further increases in effective resistance can be achieved with reduced wall thicknesses made possible by titanium alloys.

The titanium alloy IMD housings offer high resistivity that enable a rechargeable IMD device to have much better electrical performance (both power coupling and telemetry). This offers the ability to make the rechargeable device smaller, easier to recharge, and longer lasting. The high resistivity titanium alloy housing also reduces MRI heating effects. High resistivity titanium alloys have high strength as well as high resistivity. This allows the IMD housing to be stronger or thinner, or a combination of the two.

The use of metal injection molding as part of the IMD housing fabrication process overcomes the difficulty in obtaining and in forming titanium alloys as needed for IMDs. The MIM process does not need the alloy powder in order to make alloy parts. Instead, the formulation for metal injection molding is made by a mixture of pure powders in selected percentages, together with a polymer. As a result, obtaining a particular composition of alloy is greatly simplified, and is not limited by usage of particular alloys in large quantities by the aerospace industry. In addition, the MIM process allows making housings of dimensions and shapes that cannot be achieved with wrought titanium alloy sheets. The process can make housings with tight radius curvature that cannot be achieved with conventional forming techniques.

Although the present invention has been described with reference to preferred embodiments, workers skilled in the art will recognize that changes may be made in form and detail without departing from the spirit and scope of the invention. For example, although IMD housing 40 shown in FIGS. 2A-2F is formed of two housing portions 40a and 40b of generally similar shape, other housings may be formed with portions different shapes, and with more than two portions being joined together to form the housing. The selective thinning of a housing wall can include a single thinned region as shown in FIGS. 2A-2F, or can be divided into a group of smaller regions separated by portions of a thicker wall. The invention is applicable to a wide variety of IMD's, including but not limited to implantable drug infusion pumps, implantable neurostimulators, implantable cardioverters, implantable cardiac pacemakers, cochlear implants, implantable physiologic monitors, implantable sensors and others.

The invention claimed is:

1. A housing of an implantable medical device, the housing comprising:
   a first housing portion of a titanium alloy having a resistivity of greater than about 100 µOhm-cm formed by metal injection molding; and
   a second housing portion joined in a rigidly fixed relationship to the first housing portion, the second housing portion being of the titanium alloy and formed by metal injection molding.

2. The housing of claim 1, wherein at least one of the housing portions has a region of reduced wall thickness formed by a chemical removal process.

3. The housing of claim 1, wherein the first housing portion includes a region having a wall thickness of less than about 0.015 inches.

4. The housing of claim 3, wherein the second housing portion includes a region having a wall thickness of less than about 0.015 inches.

5. The housing of claim 4, wherein the first housing portion includes a first rim and the second housing portion includes a second rim, and wherein the first and second rims are welded together.

6. The housing of claim 5, wherein the first and second rims have a wall thickness of greater than about 0.015 inches.

7. The housing of claim 1, wherein the titanium alloy includes at least one of aluminum, vanadium and molybdenum.

8. The housing of claim 7, wherein the titanium alloy includes titanium, aluminum and vanadium.

9. The housing of claim 1, wherein the titanium alloy comprises a one of: a Ti6Al4V alloy, a Ti8AlMo-IV alloy, a Ti6242 alloy, an SP-700 alloy, a Ti5Al2.5Sn alloy, and a Ti3Al2V alloy.

10. The housing of claim 1, wherein the titanium alloy includes ceramic particles.

11. The housing of claim 10, wherein the ceramic particles include at least one of titanium carbide, titanium dioxide and silicon carbide.

12. The housing of claim 1, wherein the titanium alloy has a tensile yield strength of greater than about 500 Mpa.

13. The housing of claim 1, wherein the titanium alloy comprises an α Ti or near α Ti alloy.

14. The housing of claim 1, wherein the titanium alloy has a resistivity of about 100 µOhm-cm to about 220 µOhm-cm.

15. The housing of claim 14, wherein the titanium alloy has a resistivity of about 125 µOhm-cm to about 190 µOhm-cm.

16. A method for forming the housing of an implantable medical device, the method comprising:
   forming a first housing portion by metal injection molding a titanium alloy;
   selectively reducing the wall thickness of at least one region of the first housing portion;
   forming a second housing portion by metal injection molding the titanium alloy; and
   joining the first housing portion and the second housing portion by creating a metallic weld to produce the housing of the implantable medical device.

17. The method of claim 16, wherein forming the first housing portion comprises:
   injecting a mixture of metal alloy constituent particles and a polymer into a mold to form the first housing portion;
   heating the first housing portion to remove the polymer; and
   sintering the first housing portion.

18. The method of claim 17, wherein the metal alloy constituent particles include titanium and at least one of aluminum, vanadium, and molybdenum.

19. The method of claim 17, wherein the mixture further includes ceramic particles.

20. The method of claim 16, wherein selectively reducing the wall thickness is by chemical removal.

21. An implantable medical device comprising:
   a housing of at least two portions with each of the at least two portions formed of a titanium alloy having a resistivity of greater than about 100 µOhm-cm with each of the at least two portions also being formed by metal injection molding, and with each of the at least two portions being joined by a metallic weld;
   a rechargeable power source within the housing; and
   electronic circuitry within the housing and powered by the rechargeable power source.

22. The implantable medical device of claim 21, wherein the housing has a first face with a wall thickness of less than about 0.015 inches.

23. The implantable medical device of claim 22, wherein the first face has a wall thickness of about 0.008 to about 0.012 inches.

24. The implantable medical device of claim 22, wherein the first face wall thickness is formed by a chemical removal process.

25. The implantable medical device of claim 21, and further comprising:
a coil for receiving electromagnetic energy to charge the rechargeable power source, the coil positioned within the housing adjacent the first face.

26. The implantable medical device of claim 21, wherein the titanium alloy includes at least one of aluminum, vanadium and molybdenum.

27. The implantable medical device of claim 26, wherein the titanium alloy includes titanium, aluminum and vanadium.

28. The implantable medical device of claim 21, wherein the titanium alloy comprises a one of: a Ti6Al4V alloy, a Ti8AlMo-IV alloy, a Ti6242 alloy, an SP-700 alloy, a Ti5Al2.5Sn alloy, and a Ti3Al2V alloy.

29. The implantable medical device of claim 21, wherein the titanium alloy includes ceramic particles.

30. The implantable medical device of claim 29, wherein the ceramic particles include at least one of titanium carbide, titanium dioxide and silicon carbide.

31. The implantable medical device of claim 21, wherein the titanium alloy has a tensile yield strength of greater than about 500 Mpa.

32. The implantable medical device of claim 21, wherein the titanium alloy comprises an $\alpha$ Ti or near a Ti alloy.

33. The implantable medical device of claim 21, wherein the titanium alloy has a resistivity of about 100 μOhm-cm to about 220 μOhm-cm.

34. The implantable medical device of claim 33, wherein the titanium alloy has a resistivity of about 125 μOhm-cm to about 190 μOhm-cm.

* * * * *